(12) United States Patent
Takeda et al.

(10) Patent No.: US 7,465,557 B2
(45) Date of Patent: Dec. 16, 2008

(54) METHOD OF SELECTING BARLEY VARIETY, BARLEY β-AMYLASE GENE AND PROCESS FOR PRODUCING MALT ALCOHOLIC DRINK

(75) Inventors: Kazuyoshi Takeda, Kurashiki-shi (JP); Takafumi Kaneko, Nitta-gun (JP); Makoto Kihara, Nitta-gun (JP); Takashi Asakura, Nitta-gun (JP); Kazutoshi Ito, Nitta-gun (JP)

(73) Assignee: Sapporo Breweries Limited, Tokyo (JP)

( * ) Notice: Subject to any disclaimer, the term of this patent is extended or adjusted under 35 U.S.C. 154(b) by 463 days.

(21) Appl. No.: 10/490,378

(22) PCT Filed: Oct. 2, 2002

(86) PCT No.: PCT/JP02/10298

§ 371 (c)(1),
(2), (4) Date: Oct. 4, 2004

(87) PCT Pub. No.: WO03/031653

PCT Pub. Date: Apr. 17, 2003

(65) Prior Publication Data

US 2005/0053934 A1     Mar. 10, 2005

(30) Foreign Application Priority Data

Oct. 4, 2001   (JP)   ............... 2001-309036

(51) Int. Cl.
C12Q 1/68   (2006.01)
C12Q 1/40   (2006.01)
C12N 9/42   (2006.01)
C07H 21/02  (2006.01)
C07H 21/04  (2006.01)

(52) U.S. Cl. ............... 435/22; 435/6; 435/209; 536/23.1; 536/23.2

(58) Field of Classification Search ............ 435/4, 435/69.1, 183, 200; 800/3, 4, 210, 267, 276, 800/278

See application file for complete search history.

(56) References Cited

FOREIGN PATENT DOCUMENTS

| | | |
|---|---|---|
| EP | 704 540 | 4/1996 |
| JP | 0 704 540 A2 * | 4/1996 |
| JP | 8-89298 | 4/1996 |
| JP | WO 99/00514 * | 6/1997 |
| WO | 99/00514 | 1/1999 |

OTHER PUBLICATIONS

Ali et al., Normalisation of cereal endosperm EST libraries for structural and functional genomic analysis. Plant Mol. Biol. Rep., 2000, vol. 18: 123-132.*
M. Kihara, et al., "Genetic variation of β-amylase thermostability among varieties of barley, Hordeum vulgare L., and relation to malting quality", Plant Breeding, vol. 117, No. 5, XP-00904819, Nov. 1998, pp. 425-428.
Kihara M, et al., "Studies on breeding of β-amylase activity in barley. 1. Variation of themostability of β-amylase among barley varieties and indirect selection of malting quality", Breeding Science, vol. 48, No. 1, p. 153 1998(with English translation).
Youichi Tsuchiya, et al., "Identification of malting barley varieties by genome analysis", Journal of fermentation and Bioengineering, vol. 79, No. 5, pp. 429-432.
M. Kihara, et al., "Geographical variation of β-amylase thermostability among varieties of barley (Hordeum vulgare) and β-amylase deficiency", Plant Breeding, vol. 118, No. 5, pp. 453-455 Mar. 16, 1999.
Maria J. Erkkila, et al., "Allele-dependent barley grain β- amylase activity", Plant Physiol, vol. 117, No. 2, pp. 679-685, 1998.
J. K. Eglinton, et al., Journal of Cereal Science, vol. 28, pp. 301-309, article No. jc980209 May 19, 1998.
M. G. Murray, et al., Nucleic Acids Research, vol. 8, No. 19, pp. 4321-4325 Aug. 25, 1980.
G. S. Varadarajan, et al., Plant Molecular Biology Reporter, vol. 9, No. 1 pp. 6-12 1991.
Kaneko et al, Bioscience & Industry, 2001, 59(3), pp. 175-178 (w/English translation).

* cited by examiner

*Primary Examiner*—Rebecca E. Prouty
*Assistant Examiner*—Ganapathirama Raghu
(74) *Attorney, Agent, or Firm*—Oblon, Spivak, McClelland, Maier & Neustadt, P.C.

(57) ABSTRACT

A method of selecting a barley variety comprising: a heat treatment step of heat-treating a crude enzyme solution extracted from a seed of a barley (e.g., at 57.5° C. for 30 minutes); an activity-determining step of determining the enzyme activity of β-amylase in the crude enzyme solution heat-treated; and a selection step of selecting the barley variety containing a β-amylase having a residual activity of from 85 to 90% as a result of the activity determination.

1 Claim, 4 Drawing Sheets

```
                    START CODON
5' PRIMER              ↓
ATCATCCATAGCCAGCATCCACA ATG GAGGTGAACGTGAAAGGCAACTATGTCCAAGTCTACGTCATGCTCCCTGTAAGCTCCA
TCCATTCAGACCAATCGCTGAGAACCACACACTAAAACTATTTCAAGGATCTAGTGCACACATATACATTATTGTTGTACATAT
AACATTGATACTTCTTGTAAAACTCTAATTCAAAGGGTGAAGAACAAGATCTGAGGCCTCAAATGAGTATTTTATTTGTACTAA
CCTTGACTACACTTCCATTGTTGAAATAAATAAATAGCTGGACGCCGTGAGCGTGAACAA CAGG TTCGAGAAGGGCGACGAGCT
                                                              C
                                          BASE SUBSTITUTION "C" OBSERVED IN CS188
GAGGGCGCAATTGAGGAAGCTGGTAGAGG CCGG TGTGGATGGTGTCATGGTAGACGTCTGGTGGGGCTTGGTGGAGGGCAAGGG
CCCCAAGGCGTATGACTGGTCCGCCTACAAGCAGTTGTTTGAGCTGGTGCAGAAGGCTGGGCTGAAGCTACAGGCCATCATGTC
GTTCCACCAGTGTGGTGGCAACGTCGGCGACGCCGTCAACATCCCAATCCCACAGTGGGTGCGGGACGTCGGCACGCGTGATCC
CGACATTTTCTACACCGACGGTCACGGGACTAGGAACATTGAGTACCTCACTCTTGGAGTTGATAACCAGCCTCTCTTCCATGG
AAGATCTGCCGTCCAGGTTACTTTAAACCACCACTCTAGTTCTCTGATGCATATTTATATAGAAGTTCAAGATGACACCAAATA
CAAGCAAAAGGTTAAAGGTGCCAAAAACAGATAAGCAAAGAAACAAAACCTAGCTAATGAAACAGTCTAGAGCCTATCAAAAAA
AAAAAAAAAAACATCGAGAAGGTGCCTAGAGCGGATGGGTTTCGACAACCCTTTAGCTTTCATGCATCTTTTTGGGAAAGGGTGA
AAAACACCGTCCTTTAAGTCGATTGATGCAGGCAGCCTTCTATTGTTTGTAAGCTATCAGGAAATACAAAATTAATAGCTAGTT
GTCATTTTAATAGTTGTAGCAAGCTTTGATTCTTCTTTTGTGGCTGTGACAGATGTATGCCGATTACATGACAAGCTTCAGGGA
GAACATGAAAGACTTCTTGGATGCTGGTGTTATCGTCGACATTGAAGTGGGACTTGGCCCAGCTGGAGAGATGAGGTACCCATC
ATATCCTCAGAGCCACGGATGGTCGT TCCCAGGCATCGGAGAATTCATCGTGAGTG
                                                      3' PRIMER
```

METHOD OF SELECTING BARLEY VARIETY, BARLEY β-AMYLASE GENE AND PROCESS FOR PRODUCING MALT ALCOHOLIC DRINK

TECHNICAL FIELD

This invention relates to a method of selecting a barley variety with high fermentability and to a process for producing a malt alcoholic beverage utilizing the barley.

BACKGROUND ART

In the past, barley breeding has been performed by employing traditional crossing techniques. Specifically, individual varieties having different genotypes are crossed, desirable lines are selected from the obtained progeny lines based on cultivation characteristics such as agricultural characteristics, environmental adaptation, and disease resistance, and the selected lines are bred to produce genetically fixed barleys. This process needs five to six years normally, and in addition, it also requires to select only the barley variety from the genetically fixed barleys that has excellent fermentation characteristics. In order for a preferable barley for a malt alcoholic beverage to be selected, an enormous amount of time is required to be spent.

Such barley breeding requires breeders to carry it out based on their experiences. To select the barley that is believed to possess excellent fermentation characteristics, breeding needs to be done by subjective judgments of experienced breeders.

The barleys used as materials for malt alcoholic beverages (such as beer and low-malt beer) contain carbohydrases such as α-amylase and β-amylase. Carbohydrates in barley seeds are decomposed to low molecular weight sugars by the action of these carbohydrases during malting or saccharization.

In WO 99/00514 the present inventors have reported on the correlation between the property of β-amylase and barley varieties that the final apparent attenuation which represents the fraction of the portion in carbohydrates in the barley malt to be utilized in fermentation excels as the thermostability of β-amylase increases. However, with respect to the therostabilities of β-amylases for various barley varieties classified into four types, even the one with most excellent thermostability only displays a residual activity of 45 to 50% upon heat treatment at 57.5° C. for 30 minutes. No thermally stable varieties of cultivated barleys that surpass said variety have been discovered.

Eglinton et al. discovered a line in wild barleys (*H. Spontaneum*) for which the thermostability of β-amylase was high, but its utilization in breeding involved difficulties because it is a wild species. (Eglington, J. K., P. Langridge and D. E. Evans (1998) Thermostability variation in alleles of barley beta-amylase. J. Cereal Science 28: 301-309.)

DISCLOSURE OF THE INVENTION

This invention has been made in view of the problems that are inherent in the aforementioned prior art; it aims at providing a method of selecting a barley variety having a β-amylase with high thermostability for the purpose of increasing the saccharization efficiency in the production of malt alcoholic beverages.

As a result of having pursued diligent investigations to accomplish the above-stated object, the present inventors discovered a local barley variety having a β-amylase with high thermostability and found that the structural gene of the β-amylase was a novel gene, upon which this invention has been accomplished.

The method of selecting a barley variety according to this invention comprises:

a heat treatment step of heat-treating a crude enzyme solution extracted from a seed of a barley;

an activity-determining step of determining the enzyme activity of β-amylase in the crude enzyme solution heat-treated; and a selection step of selecting the barley variety containing a β-amylase having a residual activity of from 85 to 90% as a result of the activity determination.

In the heat treatment step above, preferably the crude enzyme solution is heat-treated at a predetermined temperature of from 55 to 58° C. and at a predetermined time of 10 to 60 minutes. It is particularly preferable to heat-treat the crude enzyme solution at 57.5° C. for 30 minutes.

The method of selecting a barley variety according to this invention also comprises:

a gene amplification step of amplifying a β-amylase structural gene region in the genomic DNA extracted from a barley;

a gene detection step of cleaving the β-amylase structural gene amplified in the gene amplification step with a restriction enzyme and detecting a gene fragment having a predetermined base number; and a step of selecting the barley variety based on the base number of the gene fragment detected in the gene detection step.

In the gene amplification step above, the gene region to be amplified is preferably a gene region containing the second exon of the barley β-amylase gene; and in the gene detection step, the restriction enzyme is preferably MspI. When the gene detection is carried out under these conditions, the gene fragment detected contains a 53 bp-fragment if the novel β-amylase of this invention is detected and a gene fragment having a size greater than 53 bp is detected if a known β-amylase is detected.

The barley β-amylase gene according to this invention comprises a nucleic acid sequence set forth in SEQ ID NO:1 in the Sequence Listing. The barley β-amylase gene according to this invention may also comprise a portion of the nucleic acid sequence.

The process for producing a malt alcoholic beverage according to this invention comprises:

a malting step of malting the barley selected by the method of selecting a barley variety as described above to obtain a malt;

a preparing step of saccharizing the malt to obtain a wort; and a fermentation step of fermenting the wort after addition of a yeast to the wort to obtain the malt alcoholic beverage.

This production process increases the starch-decomposing efficiency in the saccharization step and allows fermentable low molecular weight sugars to be generated in large quantities. Consequently, it will be possible to increase the fermentation efficiency in the production, to raise the saccharization temperature in the preparation step, and to carry out the production of a malt alcoholic beverage while shortening processing time and suppressing the activities of proteases.

BEST MODE FOR CARRYING OUT THE INVENTION

The preferred embodiments of this invention will be described in detail hereafter.

The method of selecting a barley variety according to this invention comprises:

a heat treatment step of heat-treating a crude enzyme solution extracted from a seed of the barley;

an activity-determining step of determining the enzyme activity of β-amylase in the crude enzyme solution heat-treated; and a selection step of selecting the barley variety containing a β-amylase having a residual activity of from 85 to 90% as a result of the activity determination.

The heat treatment step according to this invention will be first described.

The heat treatment step according to the invention is a step by which a crude enzyme solution extracted from the seeds of a barley that is subjected to selection (which will be referred to as "subject barley" hereafter).

For the seed of the subject barley according to the invention, its growth stage is not particularly limited but mature barley seeds are preferably used. Here, the barley tissue to be used is not particularly limited and, for example, endosperm tissue can be used specifically. When the endosperm tissue is used, its portion containing embryo of one seed germinates to grow and the character of β-amylase is selected in the endosperm portion. This can also be utilized in the selection of individuals during backcross generation.

The method of extracting the crude enzyme solution is not particularly limited insofar as it does not inhibit the activity of β-amylase. For example, the extraction solution using 50 mM acetic acid buffer (pH 5.5) containing 10 mM dithiothreitol for extraction is centrifuged to prepare the crude enzyme solution from the supernatant.

In the heat treatment step according to the invention, preferably the crude enzyme solution is heat-treated at a predetermined temperature of from 55 to 58° C. and at a predetermined temperature of 10 to 60 minutes. It is particularly preferable to heat-treat the crude enzyme solution at 57.5° C. for 30 minutes. These temperature and time conditions are, however, not restrictive and the treatment may be conducted under other conditions.

The activity-determining step according to this invention will be next described.

The activity-determining step according the invention is a step of determining the enzyme activity of β-amylase contained in the crude enzyme solution heat-treated.

There is no particular limitation to the method of determining the enzyme activity of β-amylase contained in the crude enzyme solution heat-treated in the heat treatment step. Techniques known in the art may be used to carry out the determination. Specifically, it may be carried out by using a Betamyl kit (Megazyme International) which is an activity-determining kit to use p-nitrophenylmaltopentaoside as substrate. Alternatively, it may be carried out by using dichlorophenyl-β-maltopentaside (Ono Pharmaceutical Co., Ltd.) as substrate and allowing this substrate to react with the crude enzyme solution at 37° C. to determine the production level of dichlorophenol. Here, in the determination of β-amylase activity it is necessary to determine the activity of a crude enzyme solution as control that has not been heat-treated.

The selection step according to this invention will be then described.

The selection step according to the invention is a step of selecting a barley variety containing β-amylase having a residual activity of from 85 to 90% as a result of the activity determination.

Specifically, the residual activity of the β-amylase derived from the subject barley is calculated based on the results from determination of β-amylase activity for the respective crude enzyme solutions extracted from the subject barley and the barley to be a control. Consequently, the barley for which the residual activity is determined to be from 85 to 90% will be selected.

The second method of selecting a barley variety according to this invention will be then described.

The second method of selecting a barley variety according to the invention comprises:

a gene amplification step of amplifying a β-amylase structural gene region in the genomic DNA extracted from a barley;

a gene detection step of cleaving the β-amylase structural gene amplified in the gene amplification step with a restriction enzyme and detecting a gene fragment having a predetermined base number; and a selecting step of selecting the barley variety based on the base number of the gene fragment detected in the gene detection step.

Specifically, a known gene of which the base sequence is already known (SEQ ID NO:2 in the Sequence Listing) is present in seed-expressed β-amylase genes (which will be referred to as "β-amylase gene"). However, the present inventors discovered a novel β-amylase gene (SEQ ID NO:1 in the Sequence Listing) differing from the known β-amylase gene at least with respect to one or more bases. The nucleic acid of SEQ ID NO:1 represents the base sequence for the second exon of the novel β-amylase gene, while the bases at positions from No. 290 to No. 688 represent the second exon of the known β-amylase gene having the base sequence set forth in SEQ ID NO:2.

The present inventors also found that the genotype of this novel β-amylase gene region is in accord with the thermostability of the β-amylase. Therefore, it will be possible to select a barley variety having a β-amylase with high thermostability by analyzing the β-amylase gene extracted from a barley following the method of selecting a barley variety according to this invention. Concretely, a restriction enzyme cleavage site exists which appears or disappears depending on the difference between the both base sequences. Thus, the β-amylase gene extracted from the subject barley is cleaved with a restriction enzyme recognizing or cleaving the restriction enzyme cleavage site. It will be possible to differentiate the barley varieties by comparing their cleavage patterns.

The gene amplification step according to this invention will be first described.

The gene amplification step according to the invention is a step of amplifying a β-amylase structural gene region in the genomic DNA extracted from the subject barley.

The method of extracting genomic DNA from the subject barley is not particularly limited and it may be performed by a technique known in the art. Specifically, extraction may be performed, for example, by the CTAB method (Murray et al., 1980, Nucleic Acids Res. 8: 4321-4325) or the ethidium bromide method (Varadarajan and Prakash 1991, Plant Mol. Biol. Rep. 9: 6-12). For the tissue from which genomic DNA is extracted, it is not limited to a barley seed, but a barley leaf, stem, root or the like may also be usable. For example, when the leaf is used, it will enable the utilization in selection of a large number of individuals during backcross generation.

The novel β-amylase gene according to this invention is a novel gene discovered by the present inventors, and it is characterized in that "C" substitutes for base "A" at the 25th position in the second exon of the barley β-amylase gene as shown in SEQ ID NO:2 in the Sequence Listing when compared to the known β-amylase gene. This base substitution generates a cleavage site of restriction enzyme MspI which otherwise has not been present in the known β-amylase gene. As a result, the cleave pattern upon cleavage of the gene amplified product with MspI is different from that in the case of the known β-amylase gene, which enables differentiation.

The method of amplifying the β-amylase structural gene is not particularly limited and it may be performed by PCR (polymerase chain reaction method), for example. The primer used in PCR is not particularly limited with respect to its base sequence insofar as it is targeted to the region with which the β-amylase gene can be amplified. Specifically, its base number is preferably from 10 to 60 consecutive bases in the β-amylase gene, and more preferably from 15 to 30 consecutive bases, for example. Generally, the GC content of the primer is preferred to be 40 to 60%. Further, it is preferred that there be no difference in Tm value between two primers. It is also preferred that no secondary structure occupy within the primers.

Preferably, the region to be amplified in the present step is a region related to the CAPS marker that the present inventors found. Specifically, there may be mentioned a region related to the CAPS marker characterized in that after the region of from translation start codon 1 to 1232 bp in the β-amylase genomic structural gene according to this invention is amplified by PCR, it is cleaved with restriction enzyme MspI to generate nucleic acid fragments of 866 bp, 313 bp and 53 bp. In addition, the region to be amplified in the gene amplification step according to the invention may be a narrower range than the region of translation start codon 1 to 1232 bp insofar as it contains the 25th base in the second exon of the β-amylase gene. Preferably, it is the second exon of the β-amylase gene, for example.

The gene detection step according to this invention will be next described.

The gene detection step according to the invention is a step of cleaving the β-amylase structural gene amplified in the gene amplification step with a restriction enzyme and detecting a gene fragment having a predetermined base number.

As stated above, the novel β-amylase gene according to this invention has a noted difference in base sequence from the known β-amylase gene. Therefore, when the amplified product is cleaved with a restriction enzyme recognizing or cleaving the different part, differences can be seen in the sizes of the nucleic fragments obtained. The restriction enzyme according to the invention is not particularly limited insofar as it recognizes or cleaves the different part. Preferably, the restriction enzyme is MspI because it has been determined to posses this function.

Figure 1:
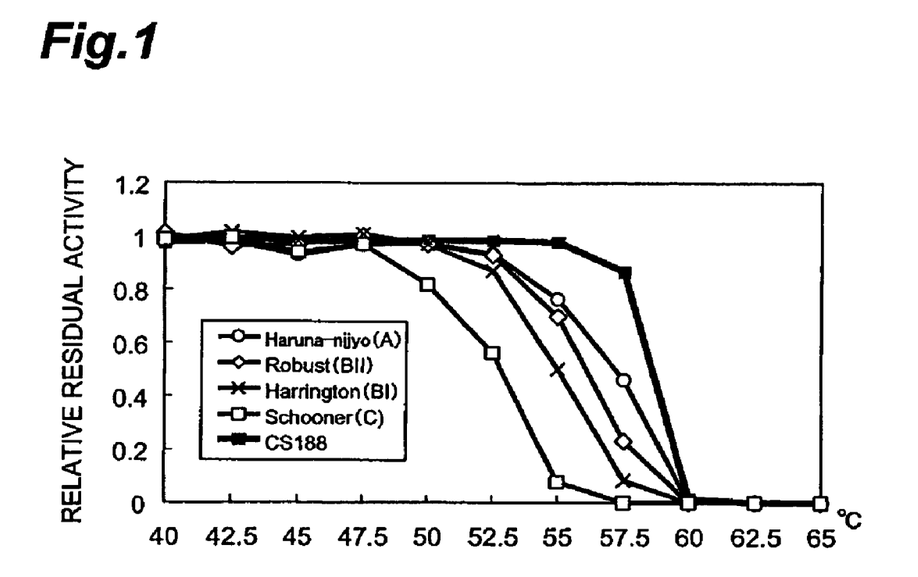
FIG. 1 is a graph showing a thermal deactivation curve of β-amylases contained in the seeds of different barley lines.
Figure 2:
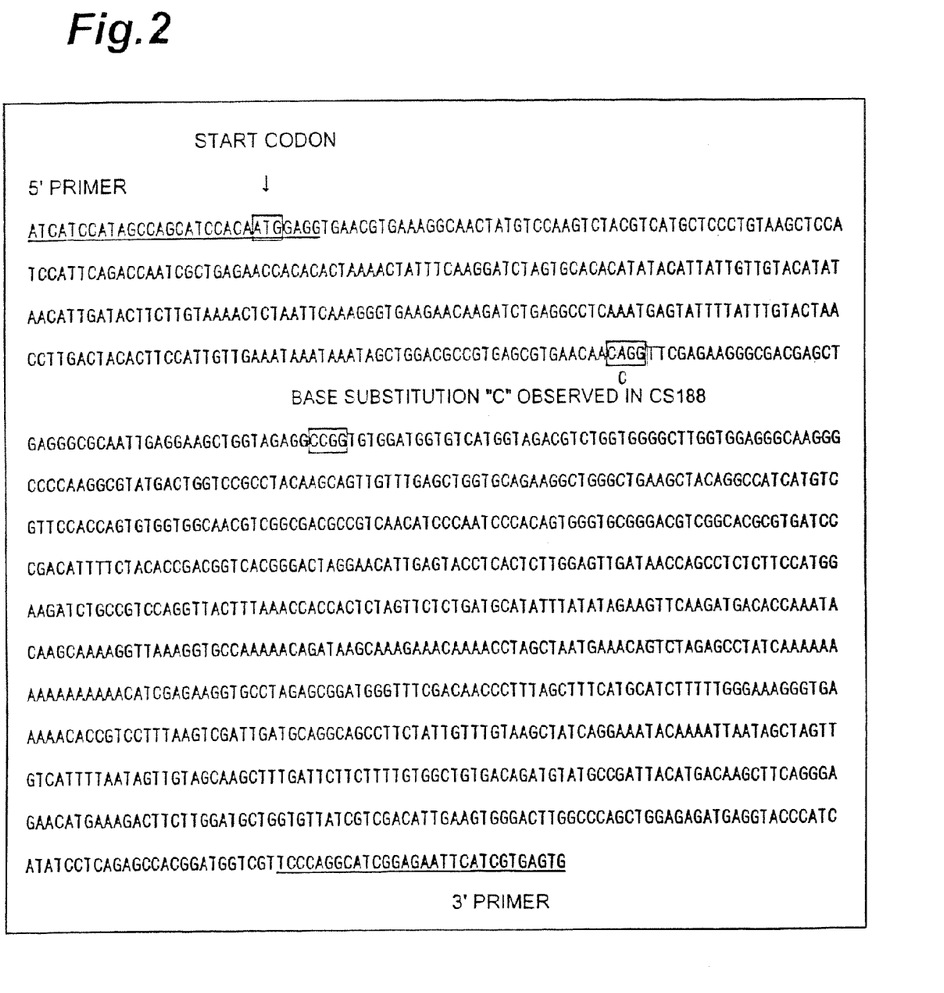
FIG. 2 is a diagram showing the base sequence (SEQ ID NO:2) of a β-amylase gene expressed in a known seed and the base sequence of the novel β-amylase gene according to this invention.

The gene fragment having a predetermined number of bases is not particularly limited as to its base number, insofar as it is a gene fragment such that when the amplified product is cleaved to nucleic acid fragments, differences can be seen in the sizes of the obtained nucleic fragments due to the presence of the different part. For example, if the region to be amplified is a region related to the CAPS marker described previously and MspI is used as the restriction enzyme, the predetermined number of bases is 866 bp, 313 bp or 53 bp. In this case, the known β-amylase gene is not cleaved with MspI because the base at position No. 314 in SEQ ID NO:2 in the Sequence Listing is "A" as previously described. In other words, as FIG. 2 shows, the known β-amylase gene according to the invention does not generate a 53 bp-nucleic acid fragment which is supposed to be generated by treatment of the novel β-amylase gene according to the invention with MspI, and only generates the two nucleic acid fragments, i.e., 366 bp and 866 bp.

The detection involved in the step is not particularly limited insofar as it is a method capable of detecting nucleic acid fragments cleaved by restriction enzymes. Specifically, detection may be performed using agarose gel electrophoresis or polyacrylamide gel electrophoresis.

The selection step according to this invention will be then described.

The selection step according to the invention is a step of selecting the barley variety based on the base number of the gene fragment detected in the gene detection step.

In the present step, the base numbers of nucleic acids detected in the gene detection step are compared and a barley variety for which a nucleic acid fragment with the desired base number is found may be selected.

The barley β-amylase gene according to this invention will be then described.

The barley β-amylase gene contains a nucleic acid having a base number of 1232 bp as shown in SEQ ID NO:1 in the Sequence Listing. The gene is genomic DNA encoding a β-amylase with high thermostability. This invention encompasses nucleic acids comprising portions of this base sequence.

It is further preferred that the nucleic acid comprising a portion of the barley β-amylase gene according to the invention satisfy the conditions described below. Specifically, the preferred is the one where "C" substitutes for "A" at 291 bp, "T" substitutes for "A" at 2410 bp, "T" substitutes for "G" at 3216 bp, "T" substitutes for "C" at 3438 bp, "T" substitutes for "C" at 3493 bp, "G" substitutes for "C" at 3598 bp, and "T" substitutes for "C" at 3696 bp, respectively as counted from the start codon of the β-amylase gene (Haruna Nijyo).

The process for producing a malt alcoholic beverage according to this invention will be finally described.

The process for producing a malt alcoholic beverage according to the invention comprises:

a malting step of malting the barley selected by the method of selecting a barley variety as described above to obtain a malt;

a preparing step of saccharizing the malt to obtain a wort; and a fermentation step of fermenting the wort after addition of a yeast to the wort to obtain the malt alcoholic beverage.

The malt alcoholic beverage according to this invention may be any alcoholic beverage produced from malt as the starting material and the malt use ratio to be used in production is not particularly restrictive (whether large or small). Specifically, there may be mentioned beer and low-malt beer (a malt alcoholic beverage with a malt use ratio of less than 25%), for example.

The malting step according to this invention will be first described.

The malting step according to the invention is a step of malting the barley selected by the method of selecting a barley variety as described above to obtain a malt. The malting method is not particularly limited provided that the thus selected barley is employed, and it may be performed by a technique known in the art. Specifically, after steeping until the steeping degree reaches 40 to 45%, the barley is allowed to germinate at 10 to 20° C. for 3 to 6 days and is roasted/dried to obtain a malt, for example.

The preparing step according to this invention will be then described.

The preparing step according to the invention is a step of saccharizing the malt to obtain a wort. Concretely, the step is further divided into the 1st to the 4th stages as described below.

Specifically, the first stage is a stage of mixing a raw material containing the malt with water for use in preparation, saccharizing the malt by heating the obtained mixture, and collecting the wort from the saccharized malt.

The malt used in the present stage is preferably obtained by allowing the barley provided with water and air to germinate, drying it and removing radicles therefrom. The malt serves as the source of enzyme required for the wort preparation, as well as simultaneously serves as the principal source of carbohydrates which are the raw materials for saccharization. To give flavor and color characteristic of a malt alcoholic beverage, the malt germinated and roasted/dried is used in the wort production. In addition, other than malt auxiliary materials such as hop, cornstarch, corn glitz, rice and sugars may be added as the raw materials. In the stage of wort preparation, a malt extract that is commercial or separately made may be mixed with water for use in preparation and the auxiliary materials may be added as necessary to obtain the wort.

The malt is added to the water for use in the preparation and then mixed. When the auxiliary materials are to be added, mixing may be performed simultaneously. The water for use in the preparation is not particularly limited and water that will be suited to the malt alcoholic beverage to be produced may be used accordingly. Saccharization may fundamentally be performed under conditions known in the art. For example, it is preferably performed by heating the mixed malt and the water for use in the preparation at from 65 to 75° C. This causes saccharization in the malt by amylase to progress. The saccharized malt liquid thus obtained is filtrated to obtain the wort.

The second stage is a stage of fermenting the wort after addition of a yeast to the wort to obtain a malt alcoholic beverage intermediate product.

The yeast used may be any of liquor yeasts that are capable of the so-called alcohol fermentation by which sugar in the wort obtained by saccharization of the malt is metabolized to generate alcohols, carbon dioxide, and the like. Specifically, there may be mentioned *Saccharomyces cerevisiae* and *Saccharomyces uvarum*, for example.

Fermentation is performed by cooling the wort obtained in the preparation step and adding the yeast thereto. The fermentation conditions are not fundamentally different from those known in the art. For example, the fermentation temperature is normally at 15° C. or lower, and preferably at from 8 to 10° C.; the fermentation time is preferably from 8 to 10 days.

The third stage is a storing stage of storing the malt alcoholic beverage intermediate product obtained in the fermentation stage.

In the present stage the fermentation liquid that has completed alcohol fermentation is transferred to an airtight tank and stored. The storing conditions are not fundamentally different from those known in the art. For example, the storing temperature is preferably at 0 to 2° C.; and the storing time is preferably from 30 to 90 days. The storage of the fermentation-completed liquid causes the remaining extract to be refermented and matured.

The fourth stage is a filtration stage of filtrating the malt alcoholic beverage intermediate product obtained in the storing stage to obtain a malt alcoholic beverage.

The filtration conditions are not fundamentally different from those known in the art. As a filtration aid, there are used diatomaceous earth, PVPP (polyvinyl polypyrrolidone), silica gel, cellulose powders, etc., for example. Filtration is carried out at a temperature of 0±1° C. In this way the malt alcoholic beverage (e.g., beer or low-malt beer) is obtained. The filtrated malt alcoholic beverage is filled in tanks, barrels, bottles or cans and shipped to the market.

The thus selected barley was used to produce the malt alcoholic beverage, and the test to measure its fermentation efficiency was conducted. Consequently, it was determined that the final apparent attenuation improved. As used herein, the final apparent attenuation represents the proportion of extract to be utilized in fermentation out of the wort extract as expressed in percentage.

Therefore, by following the process for producing a malt alcoholic beverage according to this invention and producing the malt alcoholic beverage, it will be possible to obtain fermentable sugars with high efficiency in the preparation step. The wort is then used to carry out fermentation and this allows carbohydrates in the barley to be converted into alcohol with higher efficiency compared to the conventional cases. By using the barley variety and producing the malt alcoholic beverage, it will be possible to increase the starch-decomposing efficiency in the saccharization step and to generate fermentable low molecular weight sugars in large quantities. Consequently, the fermentation efficiency can be increased, and at the same time the saccharization temperature in the preparation step can be raised. This will enable the processing time to be shortened as well as to produce the malt alcoholic beverage while suppressing the action of proteases or the like.

Furthermore, by crossing another variety of barley with the barley obtainable from the method of selecting a barley variety according to this invention, it will be possible to breed a barley containing β-amylase with high thermostability. In this case, the breeding method is not particularly limited and a technique known in the art may be used to carry out breeding.

Also, by using the barley β-amylase gene according to this invention, it is possible that a barley containing a β-amylase with high thermostability is produced by means of gene manipulation technology. The method of introducing the barley β-amylase gene into a barley is not particularly limited and it may be performed by a technique known in the art.

EXAMPLES

This invention will be described more concretely by referring to the examples and comparative examples; however, the invention is not to be limited by these examples described below.

Example 1

(Selection Method for β-amylase with High Thermostability by Heat Treatment Measurement)

A crude enzyme solution was first extracted from barley seeds. One grain of mature barley was pulverized with a hammer. Acetate buffer (50 mM, pH 5.5) containing 400 μl of 10 mM dithiothreitol was used to carry out extraction by reciprocating shaking at 4° C. for 12 hours at 100 rpm. After the extract was centrifuged at 15,000 rpm for 10 minutes, the supernatant was taken as a crude enzyme solution.

Heat treatment of β-amylase was then carried out. The crude enzyme solution was diluted to 100 fold with 50 mM MOPS buffer containing 1% BSA, and a 30 μl-aliquot was charged into a 200 μl-sampling tube and treatment was carried out at 57.5° C. for 30 minutes in a water bath.

Next, p-nitrophenylmaltopentaoside (Betamyl kit from Megazyme International) was used as the substrate to measure the β-amylase activity. Each 10 μl-aliquot respectively from the enzyme solutions in the heat-treated group and non-treated group was charged into a 200 μl-sampling tube and heated at 40° C. by remaining heat in a water bath. Then, 10 μl of substrate/enzyme solution from a Megazyme kit was added to the tube and it was allowed to react for exact 5 minutes. To this reaction solution was added 150 μl of 1% Tris solution and thereby reaction was terminated. This reaction solution (100 μl) was transferred to a multi-plate and Abs 405 was measured with a plate reader (Bio-Rad Laboratories). The value for the treated group was divided by the value for the non-treated group and this was expressed in terms of percentage: since the obtained value was from 85 to 90%, it was determined that the β-amylase enzyme of CS188 was present in the seed.

In summary, it was demonstrated that CS188 selected from the barley genetic resource had β-amylase with the thermostability far exceeding those for the barleys in the prior art (Haruna Nijyo Type A, Robust Type BII, Harrington Type BI and Schooner Type C). As used herein, when the crude enzyme solutions were heat-treated at 57.5° C. for 30 minutes, Type A, Type B and Type C were classified as follows: Type A—a residual activity of 35% or more; Type B—a residual activity of from 10 to 35%; and Type C—a residual activity of less than 10%. Type B was further divided into two types according to the isoelectric point of the β-amylase contained in barley: the type having a band of pI6.5 was classified as BI and the type having no such band was classified as BII.

Example 2

(Selection by DNA Polymorphism of β-amylase Character with High Thermostability)

Genomic DNA of the β-amylase gene extracted from CS188 was decoded by the dye-terminator method. As FIG. 2 shows, it was confirmed that the base at 291 bp from the start codon had been altered to C in the β-amylase gene isolated from CS188 as opposed to A in the case of the known β-amylase genes and the base sequence CCGG, which was a recognition site of restriction enzyme MspI, had formed.

Genomic DNAs were extracted from the spouting green leaves of CS188 and a regular variety by the SDS-propanol method. These were used as template DNAs. Each 50 μM of 5'-primer (5'-ATCATCCATAGCCAGCATCCACAATG-GAGG-3': SEQ ID NO:3) and 3'-primer (5'-CACTCACGAT-GAATTCTCCGATGCCTGGGA-3': SEQ ID NO:4) was added to 1 μl of DNA and premix ExTaq. PCR amplification was performed on a 50 μl scale (72° C.×7 min after 30 cycles at 94° C.×1 min, 55° C.×2 min, 72° C.×3 min). The obtained PCR product (5 μl) was cleaved with restriction enzyme MspI and electrophoresed on a 3% Nusieve gel (Takara Shuzo Co., Ltd.) to have band patterns observed. The annealing conditions in the PCR was set to be from 50 to 65° C.

Figure 3:
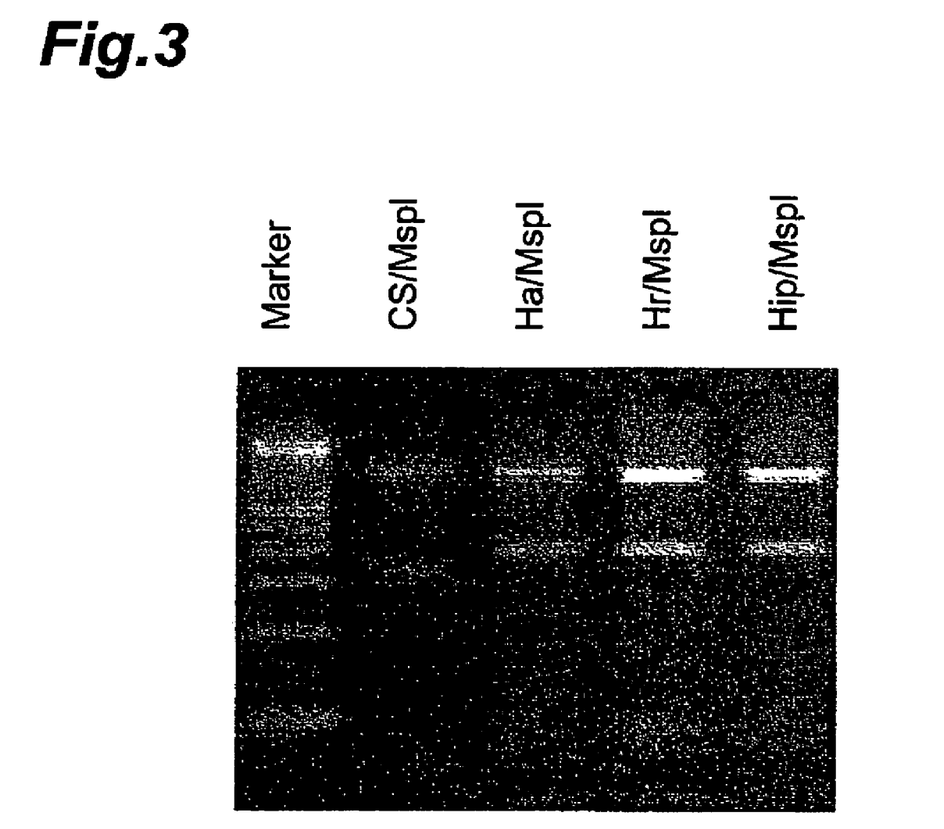
FIG. 3 is an electropherogram showing the CAPS polymorphism of β-amylase genes from the different barleys.

The β-amylase gene extracted from the regular barley generated two bands, 866 bp and 366 bp, due to an MspI restriction recognition site at around 366 bp from the 5'-end. In contrast, the CS188 type β-amylase gene generated three bands, 866 bp, 313 bp and 53 bp, because it had an MspI restriction recognition site at around 313 bp in addition to the MspI restriction recognition site at around 366 bp. As FIG. 3 shows, the electrophoretic patterns, therefore, allowed the β-amylase character with high thermostability to be selected because of the difference of the band positions of 366 bp and 313 bp. The marker used in the electrophoresis was a 100 bp-ladder DNA.

Forty-eight grains of Schooner X CS188 crossed F2 seeds were cut in halves, the portion containing embryo and the portion containing no embryo, and the thermostability of the portion containing no embryo was investigated according to the method described in Example 1. However, the heat treatment temperature was set at 58° C. DNA was extracted from the bud germinated from the portion containing embryo and the genotype of the β-amylase was studied.

Figure 4:
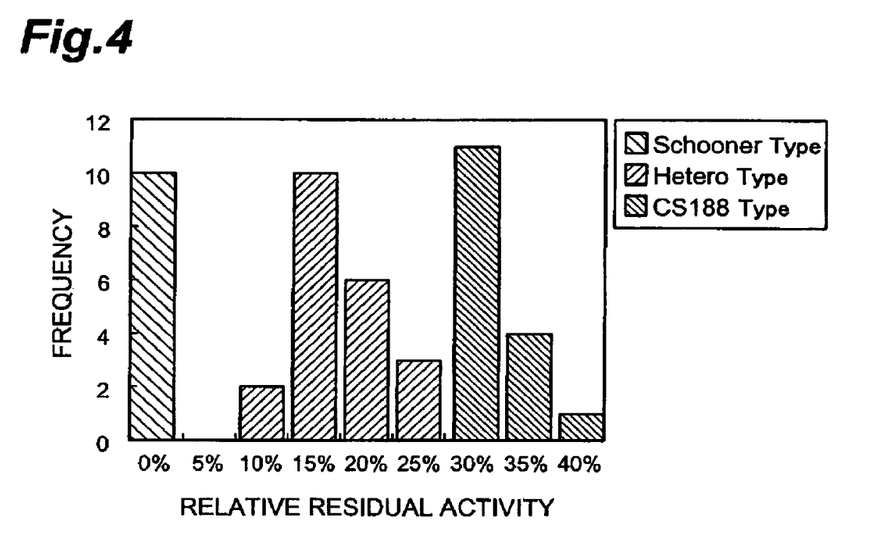
FIG. 4 is a graph showing the thermostabilies of β-amylases extracted from Schooner X CS188F2 crossed F2 seeds.

As the results are shown in FIG. 4, in all 48 individual grains the homozygous CS188 exhibited activity at the same level as did CS188, the homozygous Schooner lost its activity as did Schooner, and the heterozygous Schooner exhibited thermostability in between. Therefore, it was confirmed that the polymorphism of β-amylase structural gene could be used as the index for the selection of thermostability of β-amylase.

Example 3

(Process for Production of Malt Alcoholic Beverage)

CS188 that had been identified as the barley having a β-amylase with high thermostability and OUC57+ for which the β-amylase thermostability was type A (as control) were steeped until their steeping degrees reached 42.5%. Subsequently, germination was allowed at 15° C. for 6 days and then roasting/drying produced malts. After the malts was ground, worts were produced in a saccharization process as shown in the diagrams of FIG. 5.

Figure 5:
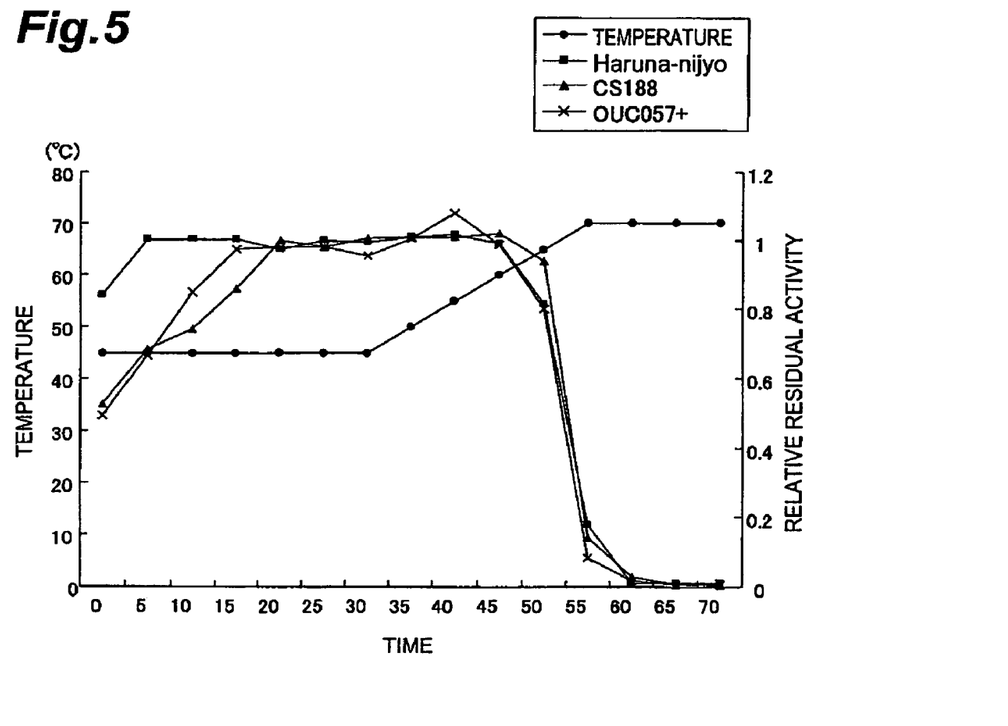
FIG. 5 is a graph showing diagrams of saccharization step in the production of malt alcoholic beverages and thermal deactivation curves of the β-amylases.

As FIG. 5 shows, the degree of deactivation of β-amylase during saccharization is such that CS188 maintained high activity until a later stage of saccharization when the temperature rose. It was thus anticipated that saccharization would proceed efficiently.

Next, a small-scale fermentation test was carried out according to the EBC standard method by using the obtained worts to determine the final apparent attenuation. Consequently, the final apparent attenuation of CS188 was 77.8%, which was higher than 77.0% for OUC057+ as the control. It was thus thought that excellent fermentation efficiency could be achieved.

INDUSTIAL APPLICABILITY

As described above, it will be possible to provide a method of selecting a barley variety having a β-amylase with high thermostability for the purpose of improving saccharization during the production of malt alcoholic beverages by utilizing the method of barley variety selection, the barley β-amylase gene, and the production process of malt alcoholic beverages according to this invention.

The invention claimed is:

1. A method of selecting a barley variety, which comprises:

heating a crude enzyme solution extracted from a seed of a barley;

determining the enzyme activity of a β-amylase in the crude enzyme solution heat-treated; and selecting a barley variety comprising a β-amylase having a residual activity of from 85 to 90% as a result of the activity determination compared to an unheated control, determining a nucleotide sequence of a gene encoding the β-amylase of the selected barley variety, and selecting the barley variety comprising a structural gene of the β-amylase comprising the sequence set forth in SEQ ID NO:1, wherein said heating of the crude enzyme solution occurs at a predetermined temperature of 55 to 58° C. and for a time of 10 to 60 minutes.

* * * * *

SEQUENCE LISTING

<160> NUMBER OF SEQ ID NOS: 4

<210> SEQ ID NO 1
<211> LENGTH: 399
<212> TYPE: DNA
<213> ORGANISM: Hordeum vulgare

<400> SEQUENCE: 1

| ctggacgccg tgagcgtgaa caaccggttc gagaagggcg acgagctgag ggcgcaattg | 60 |
| aggaagctgg tagaggccgg tgtggatggt gtcatggtag acgtctggtg gggcttggtg | 120 |
| gagggcaagg gccccaaggc gtatgactgg tccgcctaca agcagttgtt tgagctggtg | 180 |
| cagaaggctg ggctgaagct acaggccatc atgtcgttcc accagtgtgg tggcaacgtc | 240 |
| ggcgacgccg tcaacatccc aatcccacag tgggtgcggg acgtcggcac gcgtgatccc | 300 |
| gacattttct acaccgacgg tcacgggact aggaacattg agtacctcac tcttggagtt | 360 |
| gataaccagc ctctcttcca tggaagatct gccgtccag | 399 |

<210> SEQ ID NO 2
<211> LENGTH: 1232
<212> TYPE: DNA
<213> ORGANISM: Hordeum vulgare

<400> SEQUENCE: 2

| atcatccata gccagcatcc acaatggagg tgaacgtgaa aggcaactat gtccaagtct | 60 |
| acgtcatgct ccctgtaagc tccatccatt cagaccaatc gctgagaacc acacactaaa | 120 |
| actatttcaa ggatctagtg cacacatata cattattgtt gtacatataa cattgatact | 180 |
| tcttgtaaaa ctctaattca aagggtgaag aacaagatct gaggcctcaa atgagtattt | 240 |
| tatttgtact aaccttgact acacttccat tgttgaaata ataaatagc tggacgccgt | 300 |
| gagcgtgaac aacaggttcg agaagggcga cgagctgagg gcgcaattga ggaagctggt | 360 |
| agaggccggt gtggatggtg tcatggtaga cgtctggtgg ggcttggtgg agggcaaggg | 420 |
| ccccaaggcg tatgactggt ccgcctacaa gcagttgttt gagctggtgc agaaggctgg | 480 |
| gctgaagcta caggccatca tgtcgttcca ccagtgtggt ggcaacgtcg gcgacgccgt | 540 |
| caacatccca atcccacagt gggtgcggga cgtcggcacg cgtgatcccg acattttcta | 600 |
| caccgacggt cacgggacta ggaacattga gtacctcact cttggagttg ataaccagcc | 660 |
| tctcttccat ggaagatctg ccgtccaggt tactttaaac caccactcta gttctctgat | 720 |
| gcatatttat atagaagttc aagatgacac caaatacaag caaaaggtta aaggtgccaa | 780 |
| aaacagataa gcaagaaac aaaacctagc taatgaaaca gtctagagcc tatcaaaaaa | 840 |
| aaaaaaaaaa catcgagaag gtgcctagag cggatgggtt tcgacaaccc tttagctttc | 900 |
| atgcatcttt ttgggaaagg gtgaaaaaca ccgtcctta agtcgattga tgcaggcagc | 960 |
| cttctattgt ttgtaagcta tcaggaaata caaattaat agctagttgt cattttaata | 1020 |
| gttgtagcaa gctttgattc ttctttttgtg gctgtgacag atgtatgccg attacatgac | 1080 |
| aagcttcagg gagaacatga aagacttctt ggatgctggt gttatcgtcg acattgaagt | 1140 |
| gggacttggc ccagctggag agatgaggta cccatcatat cctcagagcc acggatggtc | 1200 |
| gttcccaggc atcggagaat tcatcgtgag tg | 1232 |

<210> SEQ ID NO 3
<211> LENGTH: 30

```
<212> TYPE: DNA
<213> ORGANISM: Artificial Sequence
<220> FEATURE:
<223> OTHER INFORMATION: synthetic polynucleotide

<400> SEQUENCE: 3
atcatccata gccagcatcc acaatggagg                                    30

<210> SEQ ID NO 4
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 4
cactcacgat gaattctccg atgcctggga                                    30
```